United States Patent
Aravena et al.

(10) Patent No.: US 7,291,013 B2
(45) Date of Patent: Nov. 6, 2007

(54) ORGANIC SHAPED INTERFACE FOR DENTAL IMPLANT DEVICES

(75) Inventors: Ines M. Aravena, Camarillo, CA (US); Ajay Kumar, Palmdale, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 347 days.

(21) Appl. No.: 10/610,199

(22) Filed: Jun. 30, 2003

(65) Prior Publication Data
US 2004/0121286 A1    Jun. 24, 2004

Related U.S. Application Data

(60) Provisional application No. 60/392,246, filed on Jun. 28, 2002.

(51) Int. Cl.
*A61C 8/00* (2006.01)
(52) U.S. Cl. .................................................. 433/173
(58) Field of Classification Search ......... 433/172–176
See application file for complete search history.

(56) References Cited

U.S. PATENT DOCUMENTS

| | | | |
|---|---|---|---|
| 3,732,621 A * | 5/1973 | Bostrom ..................... 433/174 |
| 4,334,865 A * | 6/1982 | Borle ......................... 433/221 |
| 5,030,095 A * | 7/1991 | Niznick ...................... 433/173 |
| 5,178,539 A * | 1/1993 | Peltier et al. ............... 433/173 |
| 5,417,568 A * | 5/1995 | Giglio ........................ 433/173 |
| 5,449,291 A | 9/1995 | Lueschen et al. |
| 5,674,069 A | 10/1997 | Osorio |
| 5,702,346 A | 12/1997 | Lazzara et al. ............. 433/173 |
| 5,779,480 A | 7/1998 | Groll et al. |
| 5,810,592 A | 9/1998 | Daftary |
| 5,873,721 A * | 2/1999 | Willoughby ................ 433/173 |
| 5,897,319 A | 4/1999 | Wagner et al. ............. 433/174 |
| 5,989,027 A | 11/1999 | Wagner et al. ............. 433/172 |
| 6,164,969 A | 12/2000 | Kinkelacker |
| 6,168,436 B1 | 1/2001 | O'Brien |
| 6,174,167 B1 | 1/2001 | Wöhrle |
| 6,217,331 B1 | 4/2001 | Rogers et al. .............. 433/173 |
| 6,217,333 B1 | 4/2001 | Ercoli |
| 6,283,754 B1 | 9/2001 | Wöhrle ....................... 433/173 |
| 6,287,115 B1 * | 9/2001 | Lustig et al. ............... 433/173 |
| 6,382,976 B1 | 5/2002 | Wagner ...................... 433/174 |
| 6,386,876 B1 | 5/2002 | Lee |

(Continued)

FOREIGN PATENT DOCUMENTS

WO    WO 9737610    10/1997

(Continued)

OTHER PUBLICATIONS

PCT International Search Report for Appln. No. PCT/US03/20494 dated Oct. 29, 2003; (6 p.).

*Primary Examiner*—John J Wilson
(74) *Attorney, Agent, or Firm*—Fitch, Even, Tabin & Flannery

(57) ABSTRACT

The present invention is generally directed to an organic implant/abutment interface for dental implants. In one illustrative embodiment, the abutment comprises a body having a distal end which has an organic shape. In another illustrative embodiment, the implant comprises having a spherical coronal end which interfaces with the abutment allowing a formation of a seal.

66 Claims, 2 Drawing Sheets

U.S. PATENT DOCUMENTS

| | | |
|---|---|---|
| 6,419,491 B1 | 7/2002 | Ricci et al. |
| 6,431,867 B1 * | 8/2002 | Gittelson et al. ............ 433/173 |
| 6,454,569 B1 | 9/2002 | Hollander et al. |
| 6,527,554 B2 | 3/2003 | Hurson et al. .............. 433/173 |
| 6,655,961 B2 | 12/2003 | Cottrell |
| 6,672,872 B2 | 1/2004 | Cottrell |
| 2001/0053512 A1 | 12/2001 | Nichinonni |
| 2003/0031981 A1 | 2/2003 | Holt |
| 2003/0068599 A1 | 4/2003 | Balfour et al. |
| 2003/0118968 A1 | 6/2003 | Massoud |
| 2003/0232309 A1 | 12/2003 | Dinkelacker |
| 2003/0234489 A1 | 12/2003 | Okada |
| 2004/0063070 A1 | 4/2004 | Morgan |

FOREIGN PATENT DOCUMENTS

| | | |
|---|---|---|
| WO | WO 00 28914 | 5/2000 |
| WO | WO 01/06944 | 2/2001 |
| WO | WO 01/78621 | 10/2001 |
| WO | WO 0243610 | 6/2002 |
| WO | WO 03005928 | 1/2003 |
| WO | WO 03047455 | 6/2003 |

* cited by examiner

ORGANIC SHAPED INTERFACE FOR DENTAL IMPLANT DEVICES

The present application claims priority to U.S. Provisional Application Ser. No. 60/392,246, filed Jun. 28, 2002, the entire contents of which is specifically incorporated herein by reference.

BACKGROUND OF THE INVENTION

1. Field of the Invention

The present invention is generally related to the field of dental implants, and, more particularly, to an organic shaped interface that may be employed with various dental implant devices.

2. Description of the Related Art

It is becoming more common to replace a missing tooth with a prosthetic tooth that is placed upon and attached to a dental implant. The dental implant serves as the artificial root in that it integrates with the jawbone. The prosthetic tooth preferably has a size and a color that mimics the missing natural tooth. Consequently, the patient has an aesthetically pleasing and structurally sound artificial tooth.

One known arrangement for a dental implant involves an implant portion, or artificial root, that is received in a hole prepared in a patient's jawbone (mandible or maxilla), and an abutment, or prosthesis support, that is securable to the implant portion and that extends beyond the gingival tissue to support a tooth prosthesis. The implant portion and the abutment are constructed as separate components that are secured together by an attachment means, such as a screw passed through the abutment and received within a threaded bore in the implant portion.

Current methods by which the prosthetic tooth and implant are completely integrated into the patient's mouth require six to ten months, and sometimes longer, because two distinct, time-consuming steps are involved. In a first surgical procedure, an incision is made in the gingival tissue to expose the alveolar bone. Following any dressing of the surface of the bone that may be necessary, a hole that is complementary in shape to the implant portion is drilled in the bone and the implant portion is inserted. A healing cap or screw is attached to the implant portion to occlude the threaded bore, and the gingival tissue is stitched closed over the implant portion to await osseointegration.

In a subsequent second surgical procedure, following osseointegration of the implant portion, the gingival tissue is again opened to expose the implant portion. The healing cap or screw is removed and replaced with a second healing cap having an outer surface corresponding in shape below the gum line to that of the abutment, but protruding slightly above the gingival tissue. The gingival tissue surrounding the second healing cap is sutured thereabout to await healing in conformity to the outer surface of the second healing cap.

After the gingival tissue has healed, the second healing cap is removed and replaced with a permanent abutment that is secured to the implant. The abutment can be configured to support a single tooth prosthesis fashioned thereon or to support a bridge structure carrying multiple tooth prostheses.

However, current abutment designs do not follow the scalloped shape of the bone surrounding the natural tooth. This natural bone architecture leads to the preservation of the soft tissue between the teeth (interdental papilla) necessary for aesthetic results. Many available implants have an unnatural shape due to the configuration of the interface between the abutment and the implant portion, i.e., a side-by-side flat or beveled interface. Such interfaces typically allow only the formation of approximately flat bone contours. Such prior art interfaces do not promote the formation of bone contours exhibiting desired facial to interdental height differences required to form the adequate papilla shape that is necessary to inhibit the formation of an unaesthetic empty space between the teeth (so-called black triangle disease).

The present invention is directed to various devices that may solve, or at least reduce, some or all of the aforementioned problems.

SUMMARY OF THE INVENTION

The present invention is generally directed to an abutment for dental implants. In one illustrative embodiment, the device comprises a body having a distal end, a portion of which is adapted to be positioned around at least a portion of a coronal end of an implant, and at least one recess formed on the distal end of the body.

In another illustrative embodiment, the abutment comprises a body having a distal end, a portion of which is adapted to be positioned around at least a portion of a coronal end of an implant, and a plurality of recesses formed on the distal end of the body.

In yet another illustrative embodiment, the abutment comprises a body having a distal end, a portion of which is adapted to be positioned around at least a portion of a coronal end of an implant, and a plurality of recesses formed on distal end of the body, wherein the plurality of recesses have a radius of curvature and are positioned on opposite sides of the body and wherein the recesses are adapted to be aligned with a bone in a patient's jaw.

In a further illustrative embodiment, the device comprises an implant, an abutment having an abutment body having a distal end, a portion of the abutment body being adapted to be positioned around at least a portion of a coronal end of the implant, and a plurality of recesses formed on the distal end of the abutment body.

BRIEF DESCRIPTION OF THE DRAWINGS

The invention may be understood by reference to the following description taken in conjunction with the accompanying drawings, in which like reference numerals identify like elements, and in which.

Figure 1:
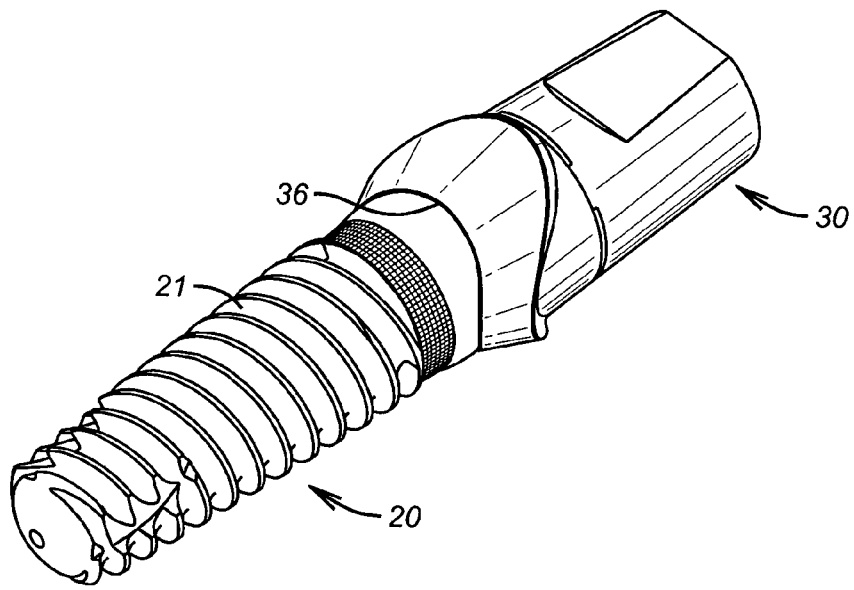
FIG. 1 is a perspective view depicting the engagement of a dental implant and an abutment in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with health-related (or human-related), system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures that are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

In general, in one aspect, the present invention is directed to various embodiments of a scalloped abutment for dental implants. As will be readily apparent to those skilled in the art upon a complete reading of the present application, the abutments described herein may be used with a variety of different surgical procedures performed to install such implants. Thus, neither the type of dental implant used nor the type of surgical procedure performed should be considered a limitation of the present invention unless such limitations are clearly set forth in the appended claims.

Aspects of the present invention will now be described with reference to the attached drawings. However, as will be understood by those skilled in the art, the present invention is not limited to the particular embodiments described or disclosed herein. As indicated in FIG. 1, an abutment 30 is adapted to engage an implant 20. The implant 20 is adapted to be securely positioned in a patient's jawbone (mandible or maxilla). In the depicted embodiment, the implant 20 has a tapered body and it is provided with a threaded exterior surface 21 that is useful in securing the implant 20 in the jawbone. In the depicted embodiment, the implant 20 is provided with self-tapping threads. In other cases, the threaded surface 21 is adapted to engage preformed threads made in a corresponding bore (not shown) in a patient's jawbone. In other designs, the implant 20 may be unthreaded. Moreover, in some embodiments, the implant 20 may have a generally cylindrical body. The implant 20 may be made from a variety of bio-compatible materials, e.g., metals, plastic, ceramic, glass or any combination thereof. In one illustrative embodiment, the implant 20 may be made of a surgical grade titanium or an alloy thereof. As will be recognized by those skilled in the art after a complete reading of the present application, the present invention may be employed with implants 20 having a variety of different configurations that may be comprised of a variety of different materials and that may be secured within the patient's jawbone by a variety of techniques. Thus, the present invention should not be considered as limited to use with any particular type or configuration of implant 20 unless such limitations are expressly set forth in the appended claims.

Figure 2:
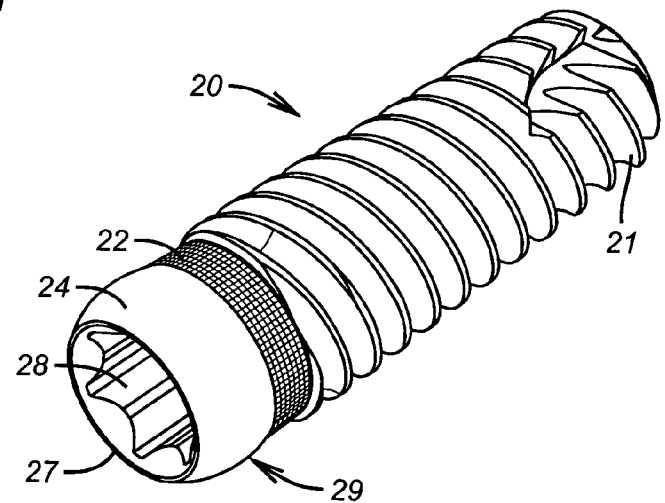
FIG. 2 is a perspective view of an illustrative dental implant in accordance with one embodiment of the present invention.

As depicted in FIG. 2, in one illustrative embodiment, the implant 20 has a coronal end 29, a transition region 22, and a bone growth promoting surface 24 on the coronal end 29 of the implant 20. The transition region 22 may have an axial length (parallel to the long axis of the implant 20) that ranges from approximately 0-2 mm. Of course, in some embodiments, the transition region 22 may be omitted, i.e., the threads could extend all the way to the bone growth promoting surface 24. In the depicted embodiment, the bone growth promoting surface 24 may have an axial length that ranges from approximately 0.5-6 mm. In some cases, the entirety of the implant 20 may have a bone growth promoting surface. In other embodiments, the bone growth promoting surface 24 may be omitted and the implant 20 may be provided with a relatively smooth surface. The bone growth promoting surface 24 may be provided by a variety of techniques. In some embodiments, the bone growth promoting surface 24 may be a roughened surface that is created by machining, grit blasting, knurling, etching, forming, etc. In other embodiments, the bone growth promoting surface 24 may be a coating comprised of, for example, peptides, bone/tissue growth factors, or a plasma sprayed coating of hydroxyapatite (HA) or the like. If employed, such a coating may have a thickness of approximately 2-20 microns. As will be recognized by those skilled in the art after a complete reading of the present application, the present invention may be employed with implants 20 that have a variety of different bone growth promoting surfaces 24 made by a variety of known techniques. The present invention may also be employed with implants 20 that do not have such a bone growth promoting surface 24. Thus, the present invention should not be considered as limited to use with implants 20 having such a bone growth promoting surface 24 unless such limitations are clearly set forth in the appended claims.

Figure 3:
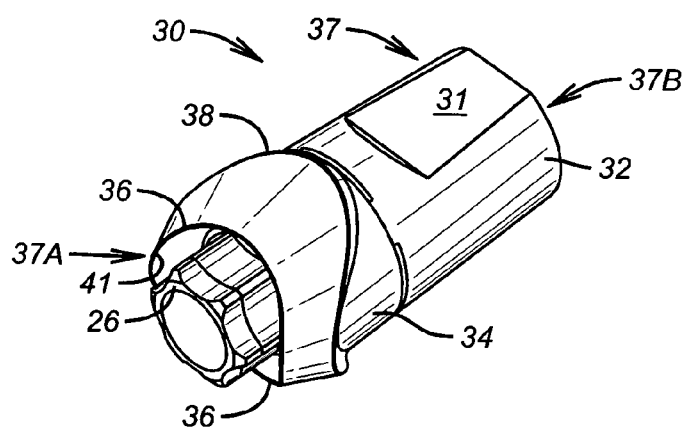
FIG. 3 is a perspective view of an abutment in accordance with one illustrative embodiment of the present invention.

Also depicted in FIGS. 2 and 3 are components 26 and 23 that, taken together, define an anti-rotation feature that prevents relative rotational movement between the implant 20 and the abutment 30. In the depicted embodiment, the anti-rotation feature is comprised of a plurality of splines 26 that are adapted to engage corresponding grooves 23 formed on the interior of the coronal end 29 of the implant 20. Of course, the anti-rotation feature may be provided by any of a variety of known techniques, internal or external key configurations, locking tapers etc. Thus, the present invention should not be considered as limited to any particular type of anti-rotation mechanism. The anti-rotational feature may be eliminated if the abutment is used in a multi-unit application.

The abutment 30 may be coupled to the implant 20 by a variety of known techniques. For example, a screw (not shown) may be provided to couple the abutment to the implant 20 via engagement with a threaded recess (not shown) positioned within the implant 20. The details of how the abutment 30 may be attached to the implant 20 are well known to those skilled in the art and, accordingly, they will not be described in any further detail so as not to obscure the present invention.

Ultimately, a tooth prosthesis (not shown) will be attached to the abutment 30. In the depicted embodiment, the abutment 30 has a body 37 that may be provided in a variety of configurations. The abutment body 37 has a distal end 37A and a proximal end 37. The distal end 37A of the abutment 30 is adapted to engage the coronal end 29 of the implant 20. In the illustrative embodiment depicted in FIG. 2, the body 37 of the abutment 30 is provided with an extension 32, a cylindrical portion 34 and a curved flange 38. A prosthetic tooth (not shown) is adapted to be positioned over the extension 32 and engage the flange 38. The prosthetic tooth may be secured to the abutment 30 by a variety of known techniques. The abutment 30 is further provided with an (optional) anti-rotation surface 31 to prevent relative rotational movement between the prosthetic tooth and the abutment. Of course, as will be understood by those skilled in the art after a complete reading of the present application, the present invention is not limited in application to use with any particular type of prosthetic tooth or device. Moreover, the present invention should not be considered as limited to the particular configuration of the abutment body 37 depicted herein, e.g., the flange 38, extension 32 and cylindrical portion 34, as such features may be varied as a matter of design choice or based upon the particular application. For example, the flange 38 may be eliminated entirely in some applications or it may be essentially a horizontal flange in other applications. The flange could also be a bevel.

Figure 4B:
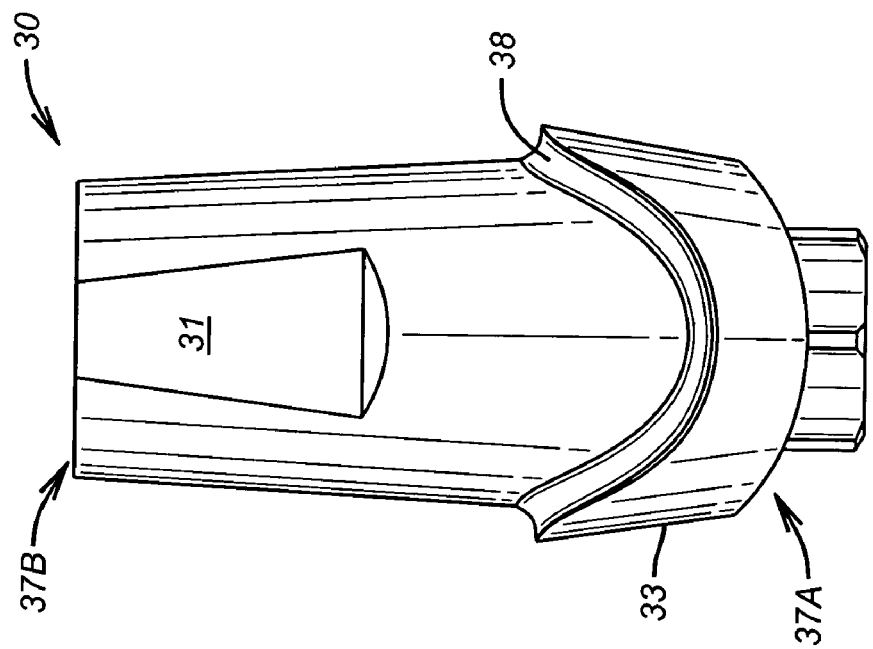
FIGS. 4A-4B are various views of an illustrative abutment in accordance with one illustrative embodiment of the present invention depicting a plurality of recesses formed on the distal end of the abutment body.
Figure 4A:
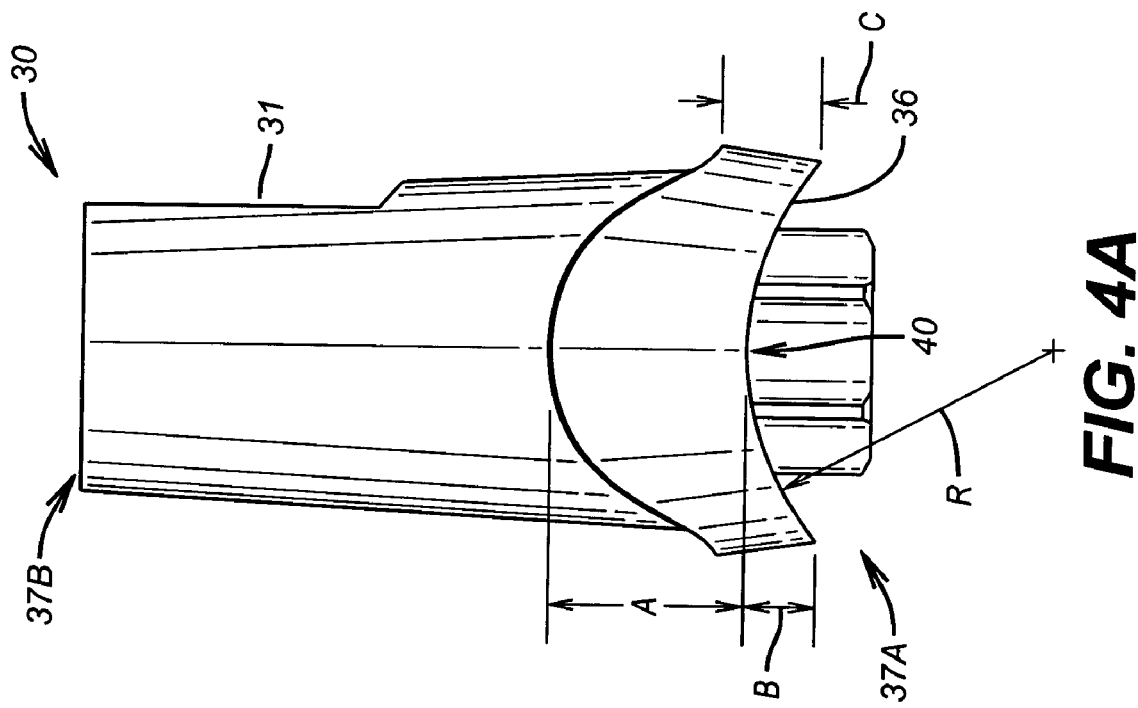

FIG. 1 depicts the abutment 30 and the implant 20 in an installed configuration. As shown in FIGS. 3 and 4A-4B, the abutment 30 is provided with a contoured or scalloped cuff 33 having a contoured or scalloped surface 36. In the depicted embodiment, the abutment 30 is provided with a plurality of recesses 40 that are positioned on approximately opposite sides of the abutment body 37. In some cases, only a single recess 40 may be employed. When installed, the recesses 40 (single or multiple) are adapted to be aligned with the bone in the patient's jaw. In one embodiment, the recesses 40 are oriented approximately 180 degrees apart, although the angular spacing relationship between the recesses may vary depending upon the particular application.

When the abutment 30 is coupled to the implant 20, at least a portion of the distal end 37A of the abutment body 37 is adapted to be positioned around at least a portion of the coronal end 29 of the implant 20. For example, in one illustrative embodiment, the scalloped cuff 33 of the abutment 30 covers a portion of the bone growth promoting surface 24 (in cases where it is employed) on the facial and lingual sides of the implant 20, but it does not cover as much of the bone growth promoting surface 24 on the sides of the implant 20 on the interdental sides of the abutment 30, i.e., between the adjacent teeth. That is, due to the recesses 40, more of the bone growth generating surface 24 is exposed in the interdental areas, thereby promoting bone growth in those areas. Accordingly, a scalloped outline is thus formed between the bone growth promoting surface 24 and the relatively smooth surfaces on the scalloped cuff 33 of the abutment 30. Thus, the scalloped or natural shape of the interface between the implant 20 and the abutment 30 (the boundary between the bone growth promoting surface and the smooth surfaces of the scalloped cuff 33) aid in maintaining the bone in the areas between the teeth. The bone in turn supports the interdental papilla. The abutment 30 may be made of a variety of bio-compatible materials, such as metals, plastic, ceramic materials, glass or any combination thereof. In one illustrative embodiment, the abutment 30 is comprised of a surgical grade titanium or an alloy thereof.

FIGS. 4A-4B are interdental and frontal views, respectively, of an abutment 30 in accordance with one illustrative embodiment of the present invention. The physical configuration of the scalloped surface 36 and the recesses 40 may vary depending upon the particular application. One illustrative embodiment of the recesses 40 is depicted in FIG. 4A. As shown therein, the dimension "A" may range from approximately 1.0-7.0 mm, the dimension "B" may range from approximately 0.5-5.0 mm and the dimension "C" may range from approximately 0.1-5.0 mm. The recesses 40 may have a radius of curvature "R" that ranges from approximately 1-8 mm (the radius should approximately follow the shape of the natural bone contours). The recesses 40 need not be symmetrical in their shape or configuration, i.e., the recesses 40 on opposite sides of the abutment 30 may have different shapes and configurations. Moreover, although the recesses 40 in the depicted embodiment have relatively smooth curved surfaces (as defined by the surface 36), the present invention should not be considered as limited to the particular curved configurations depicted in the drawings. For example, the recesses 40 could have a triangular or rectangular configuration. The recesses 40 of the abutment 30 may be formed using known machining techniques.

The present invention may be employed with a variety of different types of devices employed in producing dental implants. For example, the recesses 40 described herein may be used on healing cups, temporary restoration devices, provisional or temporary abutments, etc. In short, the recesses 40 (one or more) may be formed on the distal end of any device that is adapted to engage an implant 20 positioned in a patient's mouth. Thus, the present invention should not be considered as limited to use with permanent abutments, unless such limitations are expressly set forth in the appended claims.

In one illustrative embodiment, the coronal end 29 of the implant 20 is spherically shaped. In such an embodiment, the spherical portions of the coronal end 29 of the implant 20 may have a radius that ranges from approximately 2.0-7.0 mm, depending on the implant body size. In one illustrative embodiment, a mechanical seal may be achieved due to mechanical deformation of portions of the distal end 37A of the abutment body 37 and/or the spherical region on the coronal end 29 of the implant 20. This deformation can be expressly controlled within the elastic region of the material and maintained by selecting the appropriate materials with specific yield strengths and by determining specific spherical dimensions when the components are engaged. This would ensure that the abutment 30 will always deformed elastically once seated and would return to its pre-deformed state once is removed from the implant 20. This would ensure that the abutment 30 can be seated multiple times on the implant 20 without exhibiting any permanent plastic deformation. Also, to ensure that abutment 30 does not gall, the inside of the abutment can be coated with low friction coatings, such as DLC and Type II anodizing. Other option, would be to make one component out of softer material that could be deformed upon engagement with the other corresponding part. Due to the softness of the material, insertion forces may be reduced, and the tendency for the components to stick to one another may also be reduced. Lastly, an optional coating could be applied to prevent galling or to improve the seal between the components. The mechanical contact between the distal end 37A and the coronal end 29 of the implant 20 would be along the outermost edge of the abutment 37. This would ensure that no anaerobic bacteria can be trapped inside the implant/abutment junction and cause bone loss. In some cases, it may not be important to preserve the bone, such as posterior maxilla and mandible. In these aforementioned cases, it may not be necessary to have a complete seal.

The mechanical contact between the distal end 37A of the abutment body 37 and the coronal end 29 of the implant 20 may be varied depending upon the particular application. For example, in one aspect, at least a portion of the distal end 37A of the abutment body 37 is adapted to be positioned around at least a portion of the coronal end 29 of the implant 20. In some cases, at least a portion of the interior surface 41 of the distal end 37A of the abutment body 37 may contact the coronal end 29 of the implant 20 at one or more locations around the perimeter of the coronal end 29 of the implant 20. In other cases, there may be limited or no contact between the interior surface 41 of the distal end 37A of the abutment body 37 and the coronal end 29 of the implant 20. In other embodiments, a coronal end surface 27 (see FIG. 2) of the coronal end 29 of the implant 20 may actually contact or abut portions of the body 37 of the abutment 30, while in other cases there may be no contact between the coronal end surface 27 of the implant 20 and the abutment body 37. Of course, there may also be situations when the coronal end surface 27 of the implant 20 is in contact with at least a portion of the body 37 of the abutment 30 and where there is contact between the interior surface 41 of the distal end 37A of the abutment body 37 and the coronal end 29 of the implant 20. In summary, the manner in which the abutment 30 and the implant 20 are adapted to engage one another may vary depending upon the particular application and the manner in which mechanical loadings will be applied to the abutment 30 and/or implant 20.

In another aspect, the present invention is directed to an implant 20 having a spherical coronal end 29. The coronal end 29 may or may not be provided with a bone growth promoting surface 24. The spherical coronal end 29 of the implant 20 may be adapted to engage an abutment having a contoured cuff 33 and recesses 40 like that depicted in FIG. 3, or it may be employed with an abutment that has a straight edge surface as opposed to the scalloped surface 36 depicted in FIG. 3. The interface between the abutment 30 and the spherical coronal end 29 may be made at one or more locations around the perimeter of the spherical end. In one embodiment, the point(s) of contact are made above the centerline of the sphere.

The present invention may provided all or some of the following benefits to some degree. The present invention may promote bone support between implants because there is no need to flatten or countersink the ridge of the jawbone because the profile of the recesses 40 of the abutment 30 approximately follows the natural shape of the osseous interface, thereby eliminating or reducing the interference with bone growth provided by at least some existing implants that have a straight or flat interface between the implant 20 and the abutment 30. The present invention may also be useful in preventing or reducing bone resorption due to the presence of the recesses 40, i.e., natural interface, which acts to preserve (to at least some degree) the biological width (connective tissue and epithelial attachment lengths) and sulcus depth. The present invention may also encourage gingival support by promoting the preservation of an ideal distance (approximately 4.5 mm to 5.5 mm) between the facial gingival and the tip of the papilla. Lastly, the present invention may, in certain cases, provide a bone growth promoting surface in the areas between the teeth to promote bone growth and a smooth surface on the facial and lingual sides of the abutment to assist in dental hygiene.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A device, comprising:
   an implant having a non-scalloped, coronal end with an outer surface including a bone growth promoting surface;
   a body having a distal end receiving the non-scalloped, coronal end of the implant, the distal end covering at least a portion of the bone growth promoting surface on the non-scalloped, coronal end of the implant; and
   a scalloped surface formed on a distalmost terminal surface of said distal end of said body and forming a scalloped outline on the outer surface.

2. The device of claim 1, wherein said device includes at least one of a permanent abutment, a temporary abutment, a healing cup and a temporary restoration device.

3. The device of claim 1, wherein said scalloped surface comprises at least one recess formed on said distalmost terminal surface of said distal end, wherein said at least one recess is adapted to be aligned within a bone in a patient's jaw.

4. The device of claim 3, further comprising at least one additional recess formed on said distal end of said body.

5. The device of claim 4, wherein a plurality of recesses are positioned on approximately opposite sides of said body and wherein said recesses are adapted to be aligned with a bone in a patient's jaw.

6. The device of claim 3, wherein said at least one recess has a radius of curvature that ranges from approximately 1-20 mm.

7. The device of claim 3, wherein said at least one recess has an axial length that ranges from approximately 0.1-5.0 mm.

8. The device of claim 3, wherein said device includes an abutment and said body has a scalloped cuff formed on said distal end of said abutment, and wherein a scalloped end surface of said scalloped cuff defines at least a portion of said at least one recess.

9. The device of claim 1, wherein said distal end of said body is adapted to engage at least a portion of said coronal end of said implant around at least a portion of a perimeter of said coronal end of said implant.

10. The device of claim 1, wherein a portion of said body is adapted to engage a coronal end surface of said coronal end of said implant.

11. The device of claim 1, wherein said body is made of a material selected from the group consisting of a metal, a metal alloy, glass, ceramic and plastic.

12. The device of claim 1, wherein when said distal end of said body is engaged with said coronal end of said implant, a mechanical seal is established between said distal end of said body and said coronal end of said implant around a perimeter of said coronal end of said implant.

13. The device of claim 1, wherein said bone growth promoting surface is generally cylindrical.

14. A device with an abutment and implant combination, comprising:

a non-scalloped, coronal end of the implant having a bone growth promoting surface;
a body having a distal end receiving the non-scalloped, coronal end of the implant, the distal end covering at least a portion of the bone growth promoting surface on the non-scalloped, coronal end of the implant;
a plurality of splines connected by arcuate surfaces on said distal end of said body; and
a scalloped surface formed on a distalmost terminal surface of said distal end of said body and forming a scalloped outline on the bone growth promoting surface.

15. The device of claim 14, wherein said scalloped surface comprises at least one recess adapted to be aligned with a bone in a patient's jaw.

16. The device of claim 15, wherein said at least one recess has a radius of curvature that ranges from approximately 1-20 mm.

17. The device of claim 15, wherein said at least one recess has an axial length that ranges from approximately 0.1-5.0 mm.

18. The device of claim 15, wherein said body has a scalloped cuff formed on said distal end of said abutment, and wherein a scalloped end surface of said scalloped cuff defines at least a portion of said at least one recess.

19. The device of claim 14, wherein said distal end of said body is adapted to engage at least a portion of said coronal end of said implant around at least a portion of a perimeter of said coronal end of said implant.

20. The device of claim 14, wherein a portion of said body is adapted to engage a coronal end surface of said coronal end of said implant.

21. The device of claim 14, wherein when said distal end of said body is engaged with said coronal end of said implant, a mechanical seal is established between said distal end of said body and said coronal end of said implant around a perimeter of said coronal end of said implant.

22. The device of claim 14, wherein said bone growth promoting surface is generally cylindrical.

23. The device of claim 14, wherein said coronal end of said implant has a spherical surface.

24. A device with an abutment and implant combination, comprising:
a non-scalloped, coronal end of the implant having a bone growth promoting surface;
a body having a distal end receiving the non-scalloped, coronal end of the implant, the distal end covering at least a portion of the bone growth promoting surface on the non-scalloped, coronal end of the implant; and
a scalloped surface comprising a plurality of recesses forming a distalmost terminal surface of said distal end of said body and forming a scalloped outline on the bone growth promoting surface.

25. The device of claim 24, wherein said plurality of recesses are positioned on approximately opposite sides of said body and wherein said recesses are adapted to be aligned with a bone in a patient's jaw.

26. The device of claim 24, wherein said distal end of said body is adapted to engage at least a portion of said coronal end of said implant around at least a portion of a perimeter of said coronal end of said implant.

27. The device of claim 24, wherein a portion of said body is adapted to engage a coronal end surface of said coronal end of said implant.

28. The device of claim 24, wherein said recesses have a radius of curvature that ranges from approximately 1-20 mm.

29. The device of claim 24, wherein said recesses having an axial length that ranges from approximately 0.1-5.0 mm.

30. The device of claim 24, wherein said body has a scalloped cuff formed on said distal end of said abutment, and wherein a scalloped end surface of said scalloped cuff defines at least a portion of said recesses.

31. The device of claim 24, wherein said body is made of a material selected from the group consisting of a metal, a metal alloy, glass, ceramic and plastic.

32. The device of claim 24, wherein when said distal end of said body is engaged with said coronal end of said implant, a mechanical seal is established between said distal end of said body and said coronal end of said implant around a perimeter of said coronal end of said implant.

33. The device of claim 24, wherein said bone growth promoting surface is generally cylindrical.

34. The device of claim 33, wherein said bone growth promoting surface is comprised of a coating or a roughed surface.

35. The device of claim 24, wherein said coronal end of said implant has a spherical surface.

36. The device of claim 24, wherein said abutment is a temporary abutment.

37. The device of claim 24, wherein said abutment is a permanent abutment.

38. A device with an abutment and implant combination, comprising:
a non-scalloped, coronal end with a bone growth promoting surface;
a body having a distal end receiving the non-scalloped, coronal end of the implant, the distal end covering at least a portion of the bone growth promoting surface on the non-scalloped, coronal end of the implant, wherein the body is configured to engage the implant in one of at least three different radial orientations; and
a scalloped surface comprising a plurality of recesses formed on a distalmost terminal surface of said distal end of said body and forming a scalloped outline on the outer bone growth promoting surface, wherein said plurality of recesses have a radius of curvature and are positioned on opposite sides of said body and wherein said recesses are adapted to be aligned with a bone in a patient's jaw.

39. The device of claim 38, wherein said distal end of said body is adapted to engage at least a portion of said coronal end of said implant around at least a portion of a perimeter of said coronal end of said implant.

40. The device of claim 38, wherein a portion of said body is adapted to engage a coronal end surface of said coronal end of said implant.

41. The device of claim 38, wherein said recesses have a radius of curvature that ranges from approximately 1-20 mm.

42. The device of claim 38, wherein said recesses having an axial length that ranges from approximately 0.1-5 mm.

43. The device of claim 38, wherein said body has a scalloped cuff formed on said distal end of said abutment, and wherein a scalloped end surface of said scalloped cuff defines at least a portion of said recesses.

44. The device of claim 38, wherein said body is made of a material selected from the group consisting of a metal, a metal alloy, glass, ceramic and plastic.

45. The device of claim 38, wherein when said distal end of said body is engaged with said coronal end of said implant, a mechanical seal is established between said distal end of said body and said coronal end of said implant around a perimeter of said coronal end of said implant.

46. The device of claim 38, wherein said coronal end of said implant has a spherical surface.

47. The device of claim 38, wherein said abutment is a temporary abutment.

48. The device of claim 38, wherein said abutment is a permanent abutment.

49. A device, comprising:
- an implant configured for being mounted on a jawbone and having a coronal end with a non-scalloped outer surface, the outer surface being configured for promoting bone growth against the outer surface; and
- an abutment having an abutment body having a distal end receiving the coronal end of said implant and covering at least a portion of the outer surface; and
- a scalloped surface comprising a plurality of recesses forming a distalmost terminal surface of said distal end of said abutment body and forming a scalloped outline on the outer surface.

50. The device of claim 49, wherein said plurality of recesses are positioned on approximately opposite sides of said abutment body and wherein said recesses are adapted to be aligned with a bone in a patient's jaw.

51. The device of claim 49, wherein said distal end of said abutment body is adapted to engage at least a portion of said coronal end of said implant around at least a portion of a perimeter of said coronal end of said implant.

52. The device of claim 49, wherein a portion of said abutment body is adapted to engage a coronal end surface of said coronal end of said implant.

53. The device of claim 49, wherein said recesses have a radius of curvature that ranges from approximately 1-20 mm.

54. The device of claim 49, wherein said recesses having an axial length that ranges from approximately 0.1-5 mm.

55. The device of claim 49, wherein said abutment body has a scalloped cuff formed on said distal end of said abutment body, and wherein a scalloped end surface of said scalloped cuff defines at least a portion of said recesses.

56. The device of claim 49, wherein said abutment body is made of a material selected from the group consisting of a metal, a metal alloy, glass, ceramic and plastic.

57. The device of claim 49, wherein said implant is made from a material selected from the group consisting of a metal, a metal alloy, glass, ceramic and plastic.

58. The device of claim 49, wherein when said distal end of said abutment body is engaged with said coronal end of said implant, a mechanical seal is established between said distal end of said abutment body and said coronal end of said implant around a perimeter of said coronal end of said implant.

59. The device of claim 49, wherein said outer surface is generally cylindrical.

60. The device of claim 59, wherein said outer surface is comprised of a coating or a roughed surface.

61. The device of claim 49, wherein said coronal end of said implant has a spherical surface.

62. The device of claim 49, wherein said abutment is a temporary abutment.

63. The device of claim 49, wherein said abutment is a permanent abutment.

64. A device, comprising:
- an implant having a coronal end with a non-scalloped, bone growth promoting, spherical surface;
- an abutment having an abutment body having a distal end, a portion of said abutment body being positioned around at least a portion of a coronal end of said implant and covering at least a portion of said spherical surface; and
- a scalloped surface comprising a plurality of recesses formed on a distalmost terminal surface of said distal end of said abutment body, said scalloped surface forming a scalloped outline on the spherical surface.

65. The device of claim 64, wherein said distal end of said abutment body is adapted to engage at least a portion of said coronal end of said implant around at least a portion of a perimeter of said spherical surface of said coronal end of said implant.

66. The device of claim 64, wherein when said distal end of said abutment body is engaged with said spherical surface of said coronal end of said implant, a mechanical seal is established between said distal end of said abutment body and said spherical surface of said coronal end of said implant around at least a portion of a perimeter of said spherical surface of said coronal end of said implant.

* * * * *